United States Patent [19]

Thill et al.

[11] 4,430,079
[45] * Feb. 7, 1984

[54] FLUID DISPENSING DEVICE

[75] Inventors: Gary A. Thill, Vadnais Heights, Minn.; Jerome E. Strand, St. Joseph Township, St. Croix County, Wis.

[73] Assignee: Minnesota Mining and Manufacturing Company, St. Paul, Minn.

[*] Notice: The portion of the term of this patent subsequent to May 13, 1997 has been disclaimed.

[21] Appl. No.: 317,257

[22] Filed: Nov. 2, 1981

Related U.S. Application Data

[60] Continuation-in-part of Ser. No. 144,614, Apr. 28, 1980, Pat. No. 4,298,000, which is a division of Ser. No. 958,678, Nov. 8, 1981, Pat. No. 4,202,333.

[51] Int. Cl.³ .............................................. A61M 5/20
[52] U.S. Cl. .................................................. 604/154
[58] Field of Search .......... 128/218 A, 218 C, 218 F, 128/214.4, 215, 216, 234, 274, DIG. 12; 251/117; 604/51, 52, 151–154

[56] References Cited

U.S. PATENT DOCUMENTS

| | | | |
|---|---|---|---|
| 3,203,455 | 8/1965 | Horabin | 128/218 C X |
| 3,886,938 | 6/1975 | Szabo et al. | 128/218 A |
| 4,059,110 | 11/1977 | Wuthrich et al. | 128/218 A |
| 4,140,117 | 2/1979 | Buckles et al. | 128/218 A X |
| 4,150,672 | 4/1979 | Whitney et al. | 128/218 A X |
| 4,202,333 | 5/1980 | Thill et al. | 128/218 A |

FOREIGN PATENT DOCUMENTS

2240694 3/1973 Fed. Rep. of Germany ... 128/218 A

*Primary Examiner*—John D. Yasko
*Attorney, Agent, or Firm*—Donald M. Sell; James A. Smith; William L. Huebsch

[57] ABSTRACT

A dispensing device including a hose assembly adapted to be coupled to a conventional syringe, which hose assembly includes a length of capillary tubing through which the fluid must pass as it is delivered; and means for applying a uniform force to the plunger to provide fluid flow through the capillary tube at a slow, steady rate over a long period of time.

9 Claims, 15 Drawing Figures

FLUID DISPENSING DEVICE

CROSS-REFERENCE TO RELATED APPLICATIONS

This application is a continuation in part of U.S. Patent Application No. 144,614, filed Apr. 28, 1980, which issued on Nov. 3, 1981 as U.S. Pat. No. 4,298,000 and is in turn a Division of U.S. Patent Application No. 958,678, filed Nov. 8, 1981, which issued on May 13, 1980, as U.S. Pat. No. 4,202,333.

BACKGROUND OF THE INVENTION

The present invention relates to devices for dispensing fluids at a slow rate for a sustained period of time, and in one important aspect to such devices used for dispensing medicinal fluids into a patient's body.

The art is replete with various devices adapted for dispensing medicinal fluids at a slow sustained rate, U.S. Pat. Nos. 2,295,849; 2,602,446; 2,605,765; 3,279,653; 3,398,860; 3,468,308; 3,469,578; 3,486,539; 3,895,631 and 3,951,147 being illustrative examples.

While the fluid dispensing devices described in these patents may with varying facility be able to dispense fluids into patients, most are more complex than may be desired, many require activation or regulation by a person attaching them which if improperly done can result in the wrong dispensing rate, and most do not provide the level of protection against inadvertent improper operation of the device or tampering with the device by the patient or another that may be desired.

SUMMARY OF THE INVENTION

The present invention provides a device for dispensing fluid at a slow, uniform rate over a sustained period of time which has a simple, inexpensive structure, is easy to use, requires no regulation or adjustment by the persons using the device, and which is well-safeguarded against tampering with or inadvertent improper operation of the device.

The dispensing device comprises a hose assembly adapted to be coupled to a conventional syringe, which hose assembly comprises a length of capillary tubing through which the fluid must pass while being delivered to a patient, and means for applying a uniform force to the plunger to provide fluid flow through the capillary tube at a slow, steady rate over a long period of time (e.g., less than 60 milliliters per hour).

The rate of flow Q in cc/sec through the capillary tube can be estimated from Poiseuille's Law expressed in the equation:

$$Q = Pr^4/8ln$$

where P is the pressure drop through the tube in dynes/cm², r is the internal radius of the capillary tube in cm, l is the length of the capillary tube in cm, and n is the liquid viscosity in poise.

By solving this equation it can be found that capillary tubes of a reasonable length suitable for restricting flow to rates in the range indicated under the influence of pressures of the range of pressures easily developed in a syringe (e.g., about 69,000 to 2,068,400 dynes/cm²) can have bores in the range of about 0.0025 to 0.023 cm. With current technology it is difficult to produce capillary tubing in this size range with bore diameters which deviate less than about 10% from a nominal diameter, however. Since the rate of flow through a tube is proportional to the fourth power of its diameter, such a deviation could cause a variation of about −34% to +46% in flow rate, which would be unacceptable for most medical uses. By only using long lengths of capillary tubing, however, (i.e., capillary tubes over 2 centimeter in length) much less variation in flow rates is found between different lengths of capillary tubing than is suggested above; perhaps because diameter variations tend to cancel each other along the length of the capillary tubes. With capillary tubing of polytetrafluoroethylene sold under the trade designation "Teflon" (which is preferred) having a nominal inside diameter in the range of 0.0025 to 0.019 cm, it has been found that lengths of the capillary tubing in excess of 2 cm. normally produce flow rate variations of less than 10%, which is acceptable for medical use of the device described herein.

Hose assemblies having capillary tubes of different nominal diameters which afford different rates of fluid flow (which rates, for example, may be indicated by color coding of the hose assemblies) can be used interchangeably in the device, and the inexpensive hose assemblies can be disposed of after use to insure sanitation for medical or other uses.

One problem presented by the use of such a hose assembly is that in many instances (such as for use in introducing fluids intraveniously) prior to activating the device, air must be purged from the hose assembly to preclude air being delivered to the patient. This purging is typically done by attaching the hose asssembly to the syringe outside of the device, and manually activating the syringe until liquid has entirely filled the hose assembly; after which the syringe is placed in the device and the device is activated to deliver the liquid to the patient at the desired rate.

For hose assemblies having small diameter capillary tubing (e.g., 0.0045 to 0.01 cm) adapted to allow only very slow rates of flow (e.g. 0.5 to 15 ml/hr) it is preferred to use a first embodiment of the hose assembly that allows the capillary tubing to be bypassed to afford rapid purging of air from the hose assembly with fluid from the syringe. The first hose assembly embodiment includes a metering assembly that provides a coupler between the hose assembly and the syringe. The metering assembly includes the capillary tube and parts moveable between a metering position at which fluid flowing through the metering assembly must pass through the capillary tubing, and a purging position at which fluid propelled by manual operation of the syringe can bypass the capillary tube and flow rapidly through the metering assembly to purge the hose assembly. The device has structure that insures that the metering assembly in this first embodiment of the hose assembly is in its metering position when the dispensing device is activated to preclude operation of the device with the metering assembly in its purge position. Support means included in a frame for the device supports the metering assembly and thereby a syringe coupled to the metering assembly. The support means is specially adapted so that it will engage and support the metering assembly only when it is in its metering position.

For metering devices having larger diameter capillary tubing (e.g. over 0.010 cm) adapted to allow relatively larger rates of flow (e.g. over 15 ml/hr) one of several other embodiments of the hose asssembly can be used that have no by pass, in which embodiments the capillary tubing may extend essentially the entire length of the hose assembly, or may be positioned at the end of the hose assembly opposite the syringe. When the capillary tubing is positioned at the end of the hose assembly opposite the syringe almost all of the air passes through the capillary tube before the liquid reaches it, which, because of the extremely low viscosity of air compared to liquid, allows a fairly rapid purge rate (e.g., less than about 20 seconds). These other embodiments of the hose assembly include more conventional couplers at their ends adapted to engage the syringe, which couplers are adopted to be received in the support means of the device.

The device includes manually operated activating means which allows the coupler of the hose assembly and a syringe attached thereto to be easily inserted in or removed from the device, and which secures the syringe and coupler in the device so they may not be tampered with when the spring means is engaged with the syringe.

The activating means includes a cover which is manually moveable between open and closed positions and is coupled to the spring means to move it to a disengaged position when the cover is opened so that a coupler and a syringe attached thereto may be inserted in the support means; and to move the spring means to an engaged position at which the spring means will apply a uniform force against the plunger of the syringe to cause fluid to flow through the hose assembly when the cover is moved to its closed position at which the cover encloses the syringe and spring means. Also included are means for releasably latching the cover in its closed position at which a portion of the cover will engage the coupler and retain it in the support means. Thus access to the syringe and removal of the metering assembly or end of the hose from the support means are precluded unless the cover is opened, which opening of the cover will disengage the spring means from the syringe and stop operation of the dispensing device.

BRIEF DESCRIPTION OF THE DRAWING

The device will further be described with reference to the accompanying drawings wherein like numerals refer to like parts through the several views and wherein.

DESCRIPTION OF THE PREFERRED EMBODIMENT

Referring now to the drawing, there is illustrated a fluid dispensing device according to the present invention generally designated by the reference numeral 10.

The fluid dispensing device 10 is adapted to dispense fluid at a slow, steady rate over a prolonged period of time from a conventional syringe 12 of the type including an elongate housing 14 with an outlet tube 16 at one end, and a plunger 18 adapted to expel fluid within the syringe 12 through the outlet tube 16.

Briefly the device 10 includes a first embodiment of a hose assembly having first and second ends, and including a metering assembly 20 at its first end which serves as a coupler to couple the hose assembly to the syringe 12, and a length of flexible hose 22 shown coupled to a needle 23 via a Luer-lock fitting 21 at its second end opposite the metering assembly 20 to facilitate injecting the fluid into a patient's veins or tissues. Alternatively the hose 22 could be open-ended to facilitate insertion of the hose 22 into a patient's digestive or breathing passages or have attached thereto any shape of head via the Luer-lock fitting portion on the hose 22 or otherwise to facilitate distributing fluids to a patient's body. The hose assembly also includes a capillary tube 25 at its first end in the metering assembly 20 (FIG. 7) through which the fluid must flow to restrict flow of fluid from the syringe 12; a support frame 24 comprising spaced fork-like members 26 and 28 for supporting the metering assembly 20 and the syringe 12; and spring means 30 for applying uniform force against the plunger 18 of the syringe 12 to press it towards the fork-like members 26 and 28 and cause fluid within the syringe 12 to flow through the metering assembly 20 and hose 22.

The syringe 12 which the dispensing device 10 is adapted to receive is of a conventional type comprising the housing 14 which includes a tubular wall 34 having an open end 35, and an end wall 36 at its end opposite the open end 35 from which projects the outlet tube 16 which defines an outlet opening for the housing 14; and the plunger 18 which has one end portion positioned within and sealing against the inner surface of the tubular wall 34 and an opposite end portion projecting from the open end 35 of the tubular wall 34, and which can have fluid (typically a liquid) within the tubular wall 34 between the end wall 36 and the plunger 18.

The metering assembly 20 includes means for bypassing the capillary tube 25 so that prior to use of the device 10, air can be purged from the metering assembly 20 and hose 22 by manual operation of the syringe 12.

Figure 6:
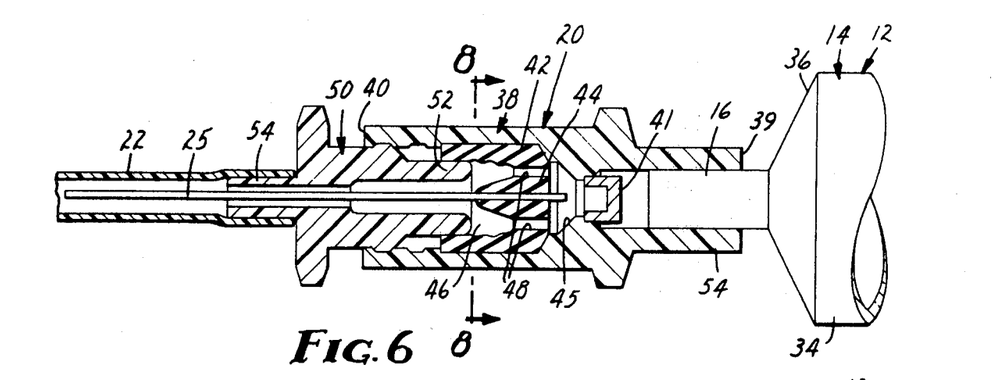
FIGS. 6 and 7 are enlarged fragmentary sectional views of the hose assembly included in the fluid dispensing device of FIG. 1 shown coupled to the syringe and shown with parts of a metering assembly included in the hose assembly positioned respectively in purging and metering positions.
Figure 7:
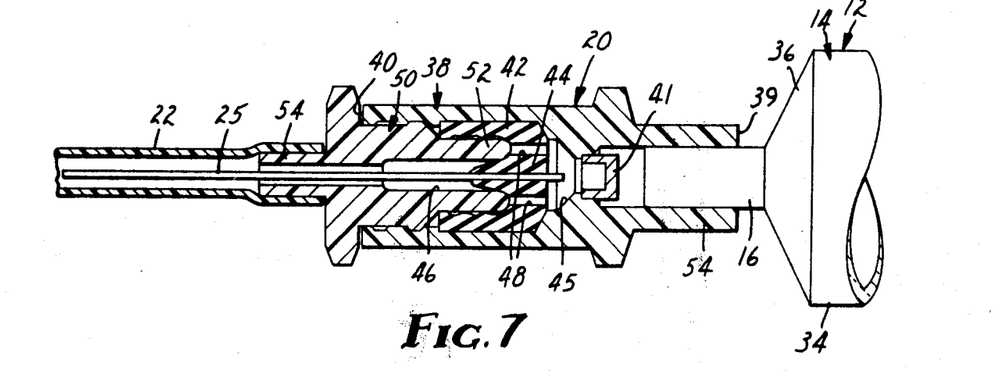
Figure 8:
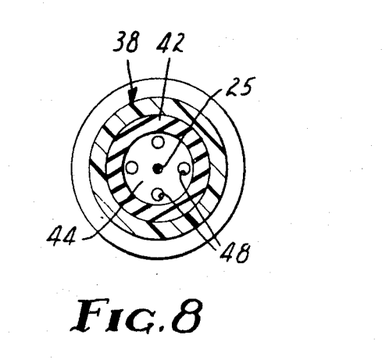
FIG. 8 is a sectional view taken approximately along line 8—8 of FIG. 6.

As is best seen in FIGS. 6 and 7, the metering assembly 20 includes a first part 38 having first and second ends 39 and 40 and a through opening between the ends 39 and 40 having a portion adjacent its first end 39 adapted to frictionally receive the outlet tube 16 on the syringe 12 to attach the syringe 12 and metering assembly 20 together. A sintered metal filter 41 is fixed to the first part 38 within its through opening and adjacent its first end 39, and a cup-like seal 42 is fixed to the first part 38 within its through opening adjacent and opening toward its second end 40. The seal 42 provides a transverse wall 44 in the through opening defining inlet and outlet chambers 45 and 46 within the first part 38 on opposite sides of the transverse wall 44. The transverse wall 44 has a plurality of through orifices 48 (FIG. 8) communicating through the tranverse wall 44 between the chambers 45 and 46. One end portion of the capillary tube 25 is fixed in and extends through the transverse wall 44 and communicates with the inlet chamber 45, whereas the other end portion is unsupported and extends through the metering assembly 20 and into the hose 22 attached thereto. The metering assembly 20 also includes a second part 50 which has a through opening and has an annular tubular portion 52 sealably and movably mounted within the first part 38 for movement relative to the first part 38 between a purging position of the parts 38 and 50 at which the annular portion 52 is spaced from the orifices 48 so that fluid can flow between the chambers 45 and 46 through the orifices 48 (FIG. 6), and a metering position with the annular portion 52 of the second part 50 seated in the cup-like seal 42 and blocking the orifices 48 (FIG. 7) so that fluid in the inlet chamber 45 can pass the transverse wall 44 only through the capillary tube 25. Thus prior to insertion of the metering assembly 20 and attached syringe 12 into the frame 24, the parts of the metering assembly 20 may be positioned in their purging position to afford rapid manual purging of fluid through the metering assembly 20, hose 22, and needle 23 by manual operation of the syringe 12.

Means are provided in the device for insuring that the parts 38 and 50 of the metering assembly 20 are in their metering position when the metering assembly 20 is inserted in the dispensing device 10, thereby precluding operation of the dispensing device 10 with the metering assembly 20 in its purge position. Each of the parts 38 and 50 has a distal end portion 54 which is smaller in cross sectional area than its portion adjacent the other part 38 or 50. The slots in the fork like members 26 and 28 are sized so that they will only receive the distal end portions 54 of the parts 38 and 50. Also the pairs of fork-like members 26 and 28 are spaced sufficiently close that the distal end portions 54 will be separated by too great a distance and will not align with the fork like members 26 and 28 unless the parts 38 and 50 of the metering assembly are in their telescoped together metering position, thus precluding operation of the device 10 with the parts 38 and 50 of the metering assembly 20 in their extended purging position.

Also the device 10 includes activating means manually operated by movement of a cover 53 coupled to the spring means 30 for allowing the syringe 12 and attached hose assembly to be easily inserted in or removed from the device 10 by moving the spring means 30 to a disengaged position relative to the syringe 12 when the cover 53 is opened, and by moving the spring means 30 to an engaged position against the plunger 18 of the syringe 12 when the cover 53 is closed, and means for securing the syringe 12 and hose assembly in the device 10 when the cover 53 is closed so that they may not be tampered with when the spring means is applying a uniform force to expel fluid from the syringe 12.

The frame 24 includes an elongate bar-like base portion 55 at one end of which is fixed a support member 56 including the spaced fork-like members 26 and 28 which are disposed so that they will position the syringe 12 attached to the metering assembly 20 received in the fork-like members 26 and 28 over and parallel to the base portion 55. The bar-like base portion 55 has upstanding opposed generally L-shaped rails 58 along its edges between which a hollow block 60 is mounted for movement longitudinally of the base portion 55 via four rollers 62 projecting from the edges of the block 60 adjacent the base portion 55. A plate-like slide 64 is also mounted between the rails 58 for sliding movement longitudinally of the base portion 55 between the block 60 and the member 56. A spring 66 of the type having the registered tradename "Neg'ator" has a portion 68 coiled about a hub 69 rotatably mounted within the block 60 on a shaft 70, and a straight end portion 71 extending from the block 60 to the slide 64 where it is attached by a rivet 72. The "Neg'ator" spring 66 provides a constant force attempting to wrap the entire length of the spring 66 onto its coiled portion 68, and thus provides a constant force biasing the block 60 toward the slide 64.

Figures 1, 2:
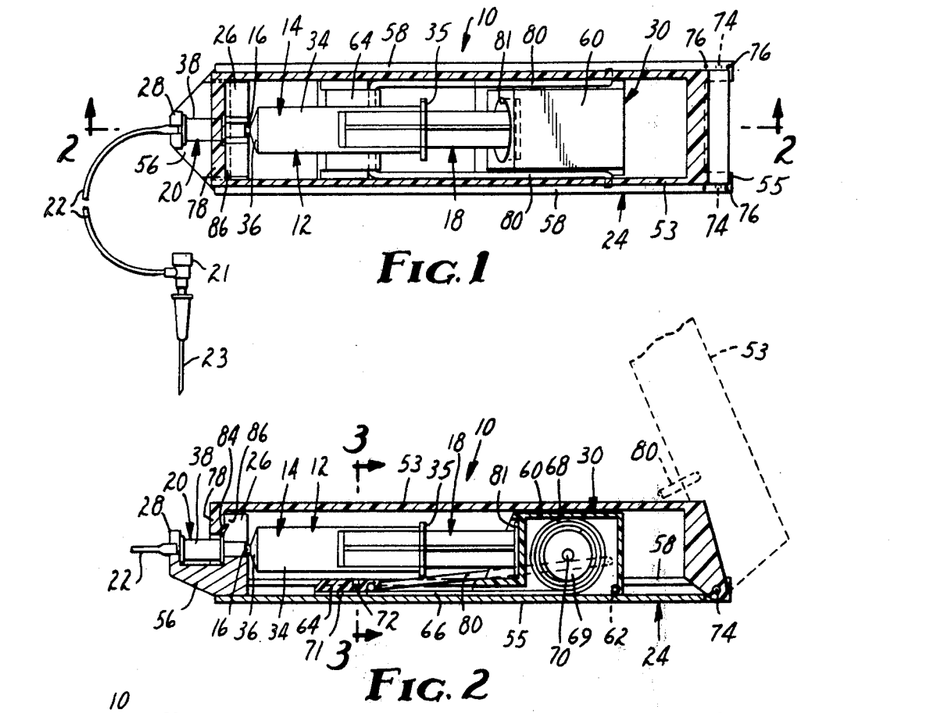
FIG. 1 is a horizontal sectional view of a fluid dispensing device according to the present invention having inserted therein a syringe from which fluid is to be dispensed and including a first embodiment of a hose assembly.
FIG. 2 is a sectional view taken approximately along line 2—2 of FIG. 1.
Figure 3:
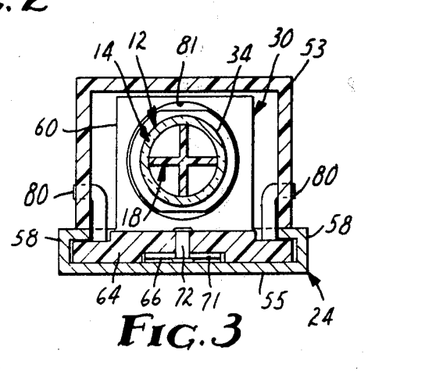
FIG. 3 is an enlarged sectional view taken approximately along line 3—3 of FIG. 2.
Figure 4:
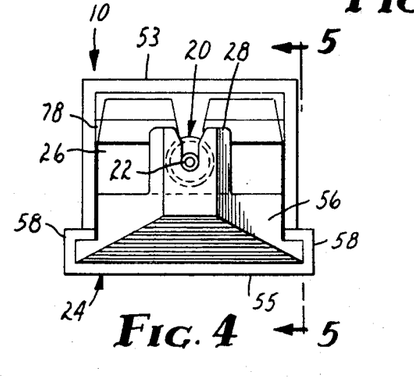
FIG. 4 is an enlarged end view of the fluid dispensing device of FIG. 1.
Figure 5:
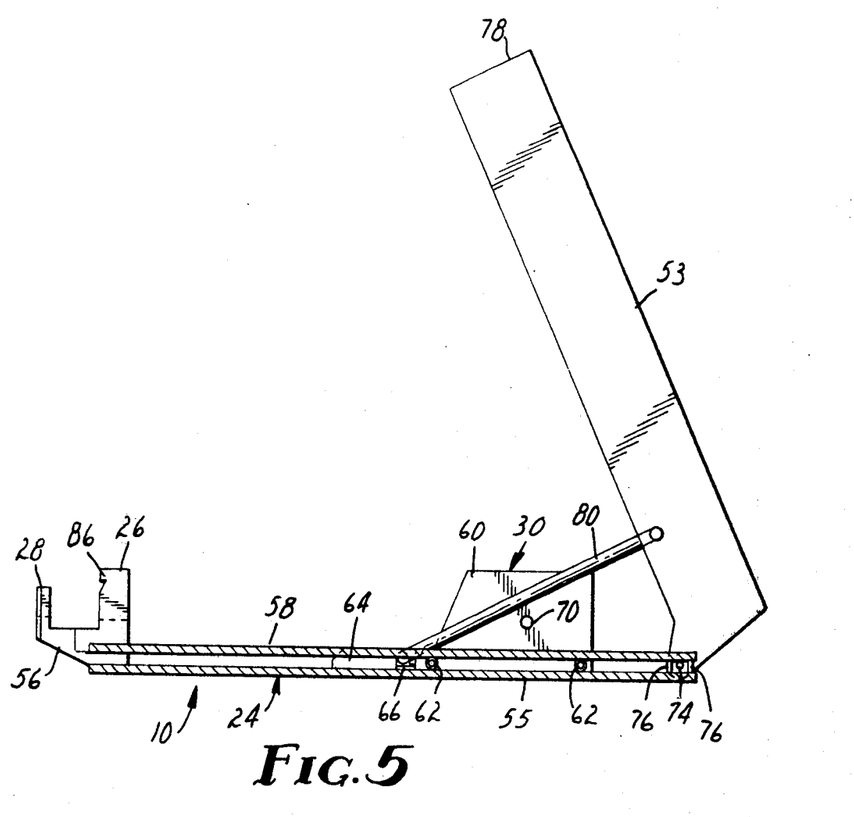
FIG. 5 is a sectional view taken approximately along line 513 5 of FIG. 4 except that a cover for the fluid dispensing device is open, and the hose assembly and the syringe are not inserted in the device.

The cover 53 is a rectangular box-like member of rigid transparent plastic material (preferably polysulfone) having an open side disposed adjacent the base portion 55 and having opposite outwardly projecting trunnions 74 on its end opposite the support member 56 which are pivotably mounted between the rails 58 and two pins 76 spaced along each of the rails 58 to afford pivotal movement of the cover 53 from an open position spaced from the base member 55, block 60 and syringe 12 (FIG. 5); and a closed position adjacent the base member 55 enclosing the block 60 and the syringe 12 therebetween, and with an edge portion 78 of the cover 53 against the metering assembly 20 received in the fork-like members 26 and 28 to preclude their removal (FIG. 2), at which closed position the cover 53 will be retained by releasable latch means later to be explained. Parallel links 80 are pivotally mounted at their ends between the cover 53 and the slide 64, and are sized and disposed so that moving the cover 53 to its open position (FIG. 5) will move the slide 64 and block 60 to a position sufficiently spaced from the fork-like members 26 and 28 that the metering assembly 20 and attached syringe 12 may be inserted in or removed therefrom; and that moving the cover 53 to its closed position (FIG. 2) will move the slide 64 adjacent the support member 56 so that when the syringe 12 and attached metering assembly 20 are supported from the fork-like members 26 and 28, the block 60 will engage the plunger 18 on the syringe 12 during such movement with the end of the plunger received in a centering pocket 81 in the adjacent face of the block 60. Such engagement will cause the slide 64 to separate from the block 60 in opposition to the spring 66 so that while the cover 53 is closed, the spring 66 will apply a constant force against the plunger 18. Also while the cover 53 is closed, the edge portion 78 rests transversely against the metering assembly 20 and precludes its removal from between the fork-like members 26 and 28.

The means for releasably latching the cover 53 in its closed position comprises transverse mating hook-like lips 84 and 86, one of which lips 84 is a part of the cover 53 adjacent its edge portion 78, and the other of which lips is a part of the fork-like member 26 adjacent its distal end; the spring 66; and a spacing between the pins 76 that allows limited longitudinal movement of the cover 53 relative to the base portion 55 of the frame 24. When the cover 53 is being moved to its closed position and after the block 60 engages the plunger 18 of the syringe 12, the force applied by the spring 66 between the separated block 60 and slide 64 via the links 80 will press the trunnions 74 on the cover 53 against the pins 76 oppposite the support member 56. As the cover 53 approaches its closed position, cam surfaces on the lips 84 and 86 engage to move the center portion of the cover 53 toward the support member 56 and allow the hook-like lips 84 and 86 to pass each other, whereupon the spring 66 again moves the center portion of the cover 53 away from the support member 56 to engage the lips 84 and 86 as the cover 53 reaches its fully closed position. Opening the cover 53 then requires sliding it longitudinally toward the support member 56 against the bias of the spring 66 to disengage the lips 84 and 86 before the cover can be pivoted to its open position, which opening operation is not apparent from a casual inspection of the closed cover 53 and could deter unauthorized deactivation of the device 10. Alternately the means for latching the cover 53 in its closed position could be a more conventional self-latching push button release latch between the cover 53 and base portion 55.

As an example of the use of the fluid dispensing device 10, a person first fills the syringe 12 with a fluid to be dispensed. Next he moves the parts 38 and 50 of the metering assembly 20 to their extended purging position (FIG. 6), attaches the metering assembly 20 to the syringe 12, and manually activates the syringe 12 so that fluid flows rapidly through the orifices 48 in the metering assembly 20 and purges air from the metering assembly 20 and hose 22. Next the user telescopes the parts 38 and 50 of the metering assembly 20 together to their metering position to block the orifices 48 so that fluid can flow through the metering assembly only via the capillary tube 25, and presses the metering assembly between the fork-like members 26 and 28 with the syringe 12 projecting over the base portion 55. The user then couples the part of the fitting 21 on the hose 22 with the part on the needle 23 or a cannula (not shown) which he has previously inserted in a patient's vein or tissues, and moves the cover 53 toward its closed position so that the cover 53 via the links 80, slide 64, and spring 66 moves the block 60 into engagement with the plunger 18 on the syringe 12, after which the slide 64 is separated from the block 60 so that the spring 66 will apply a force against the plunger 18. Further movement of the cover 53 to its closed position will cause the lips 84 and 86 on the cover 53 and fork-like members 26 to cam past each other whereupon the spring 66 will maintain the lips 84 and 86 in engagement to latch the cover 53 closed. In this condition, the "Neg'ator" spring 66 will continue to apply a uniform force to cause fluid to flow at a slow uniform rate from the syringe 12 through the capillary tube 25, hose 22 and needle 23 or cannula into the patient. During this time the device 10 can be positioned in any attitude or carried on the patient to afford ambulation without affecting the fluid dispensing rate. Also tampering with the syringe 12 or metering device 20 while the fluid is being dispensed is precluded since the syringe 12 is enclosed by the cover 53, and the metering device 20 is locked between the fork-like members 26 and 28 by the edge portion 78 of the cover, and anyone attempting to gain access to either the syringe 12 or metering device 20 will have to open the cover 53, thereby deactivating the device 10.

Referring now to FIGS. 9 through 13 there is shown a second embodiment of a hose assembly 90 that can be used and included in the dispensing device 10, which hose assembly embodiment 90 is particularly useful where it is desired to use the device for relatively large rates of fluid delivery (e.g. over 15 ml/hr).

Figure 9:
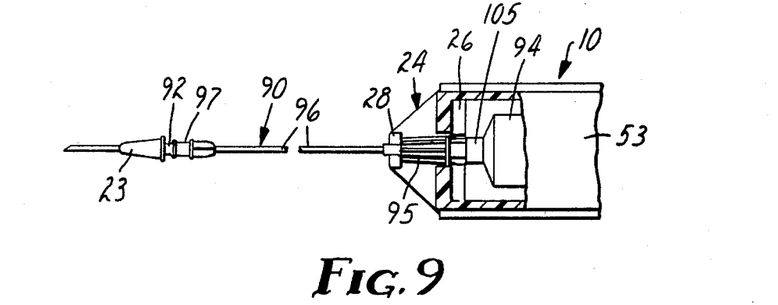
FIG. 9 is a fragmentary horizontal view of the dispensing device of FIG. 1 but which includes a second alternate embodiment of a hose assembly.
Figure 10:
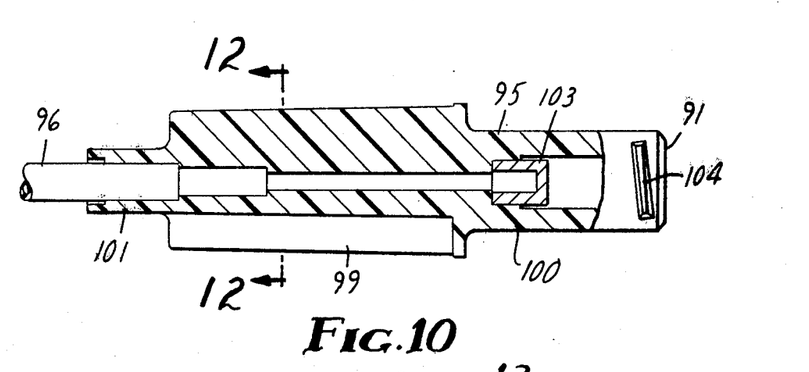
FIG. 10 is an enlarged fragmentary sectional view of a first end portion of the hose assembly shown in FIG. 9.
Figure 11:
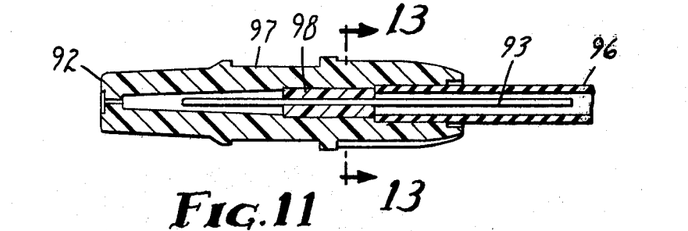
FIG. 11 is an enlarged sectional view of a second end portion of the hose assembly shown in FIG. 9.
Figure 12:
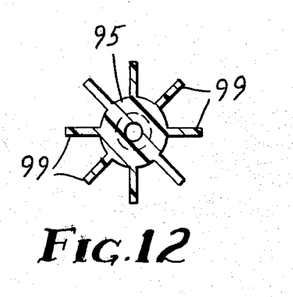
FIG. 12 is a sectional view taken approximately along lines 12—12 of FIG. 10.
Figure 13:
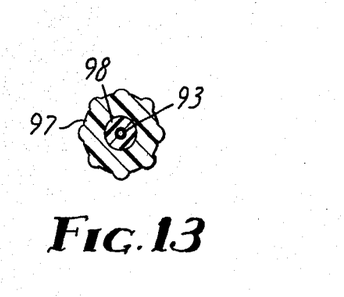
FIG. 13 is a sectional view taken approximately along lines 13—13 of FIG. 11.

Generally, the hose assembly 90 has first and second ends 91 and 92 respectively, and defines a passageway between the ends, with at least a portion of the passageway being defined by a capillary tube 93 having an inside diameter of over about 0.01 cm and a length of at least 2 cm, and has a coupler 95 at its first end 91 adapted for releasable attaching the hose assembly 90 to the housing of a syringe 94 with an outlet opening of the syringe 94 communicating with the passageway.

The hose assembly 90 includes a hose 96 having one end received and adhered in a bore through the coupler 95, and its opposite end received and adhered in a bore through a Luer-lock fitting 97 shown coupled to a needle 23 in FIG. 9. The fitting 97, of course could have its outer surface adapted to engage any desired structure, or could be adapted to be inserted into a patients digestive or breathing passages without being attached to anything, such as by removing all projecting ridges. The capillary tube passes through a soft resilient cylindrical plug 98 compressed within the bore of the fitting 97, with a portion of the capillary tube extending into the hose 96. The plug 98 provides sealing means for preventing movement of fluid around the capillary tube 93 so that all of the fluid must pass through the capillary tube 93 to regulate its flow rate.

The coupler 95 has a central portion with an outer diameter defined by radially projecting axially extending fins 99, and opposite end portions 100 and 101 of a diameter less than that of its central portion adapted to be received in the slots in the spaced fork-like members 26 and 28 of the support frame 24 for the device 10 with the fins 99 therebetween. The fins have approximately the same outside diameter as the central portion of the metering assembly 20 so that closing the cover 53 of the device 10 will lock the coupler 95 in the device 10 in the same manner described above with respect to the metering device 20.

A sintered metal filter 103 is positioned across the bore through the coupler 95, and the end of the coupler 95 opposite the hose 96 can optionally, as illustrated, have projecting angled wings 104 adapted to be engaged by a rotatable locking collar 105 around an outlet tube on the type of syringe 94 illustrated, but which syringe 94 otherwise has essentially the same structure as the syringe 12 described above.

The use of the device 10 with the hose assembly 90 is similar to its use with the hose assembly described above with respect to FIGS. 1 through 8. A user first fills the syringe 94 with a fluid to be dispensed. Next he attaches the coupler 95 to the syringe 94 via the locking collar 105, and manually activates the syringe 94 so that fluid flows through and purges air from the hose assembly 90. If the fluid in the syringe 12 is liquid, the purging will still occur at a rather rapid rate, since only air has to pass through the capillary tube 93 until the purging is almost complete. Next the user positions the coupler 95 between the fork-like members 26 and 28 with the syringe 94 projecting over the base portion 55 and proceeds to use the device 10 in the same way described above with respect to the first embodiment of the hose assembly.

Figure 14:
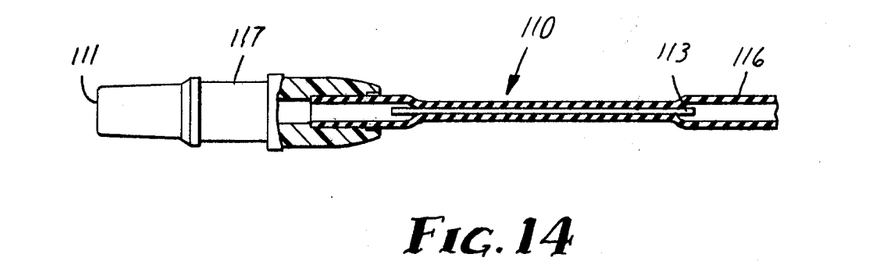
FIGS. 14 and 15 are fragmentary sectional views of third and forth alternate embodiments respectively of hose assemblies that can be used in the dispensing device of FIG. 1.

Referring now to FIG. 14 there is shown a third embodiment of a hose assembly 110 that can be included in the dispensing device 10; which hose assembly 110 like the hose assembly 90 is particularly useful where it is desired to use the device for relatively large rates of fluid delivery.

Generally, the hose assembly 110 has a first end (not shown) and a second end 111, and defines a passageway between the ends, with at least a portion of the passageway being defined by a capillary tube 113 having an inside diameter of over about 0.01 cm and a length of at least 2 cm; and has a coupler (not shown) at its first end adapted for releasable attaching the hose assembly 110 to the housing of a syringe with the outlet opening of the syringe communicating with the passageway, which coupler is essentially the same in structure as the coupler 95 of the hose assembly 90.

The hose assembly 110 includes a hose 116 having one end received and adhered in a bore through the coupler and its opposite end received and adhered in a bore through a Luer-lock fitting 117. The hose 116 is made of a heat shrinkable material, and has a portion closely adjacent the fitting 117 shrunk around the capillary tube 113 to provide sealing means for preventing movement of fluid around the capillary tube 93 so that all of the fluid must pass through the capillary tube 93 to regulate its flow rate.

Because of the location of the capillary tube 113 adjacent the second end 111 of the hose assembly 110, the hose assembly 110 provides the same advantage of quick purging without moving parts described above for the hose assembly 90.

Figure 15:
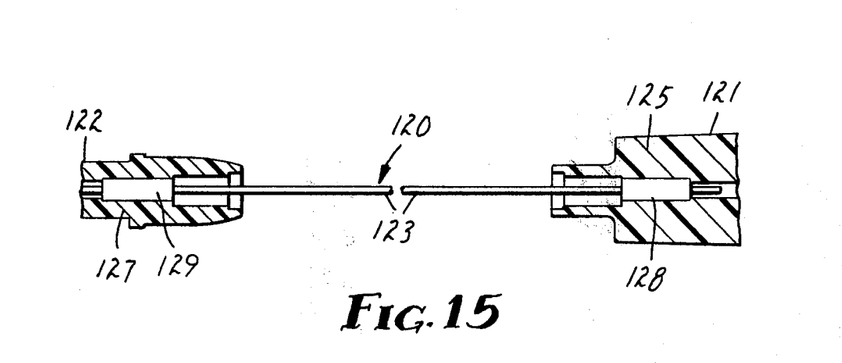

Referring now to FIG. 15 there is shown a fourth embodiment of a hose assembly 120 that can be used and included in the dispensing device 10; which hose assembly 120 like the hose assemblies 90 and 110 is particularly useful where it is desired to use the device for relatively large rates of fluid delivery.

Generally, the hose assembly 120 has first and second ends 121 and 122 respectively, and defines a passageway between the ends, with at least a portion of the passageway being defined by a capillary tube 123 having an inside diameter of over about 0.01 cm and a length of at least 2 cm; and has a coupler 125 at its first end 121 adapted for releasable attaching the hose assembly 120 to the housing of a syringe with the outlet opening of the syringe communicating with the passageway, and an outer periphery shaped essentially the same as that of the coupler 95 so that the coupler 125 will be similarly received in the spaced fork-like members 26 and 28 of the support frame 24 for the device 10.

The capillary tubing 123 in the hose assembly 120 extends between the coupler 125 and a Luer-lock fitting 127 (normally about 45 cm in length). Both ends of the capillary tube 123 pass through soft resilient cylindrical plugs 128 and 129 compressed respectively within bores of the fitting 127 and the coupler 125 to secure the ends of the capillary tube 123 thereto.

Purging of such a hose assembly in the manner described above proceeds quite rapidly because of the relatively small amount of air that must be displaced.

The present invention and its use have been explained with respect to one general type of medical use. The device may, however, be used in ways other than that indicated both for medical or other uses. For example, one or more of the devices 10 may be used to dispense fluids into a standard intravenous administration set. Also, the fluid dispensing device 10 may be used in industrial applications such as to introduce chemicals such as a catalyst into fluids moving through a continuous process, or for other uses where a small continuous supply of fluids is needed. Thus the scope of the invention should not be limited by either the structure or use of the embodiment described herein, but should be determined only by the scope of the dependent claims.

What is claimed is:

1. A fluid dispensing device adapted for engaging a fluid-filled syringe to dispense fluid from the syringe at a slow, steady rate, said syringe being of the type comprising an elongate housing including a tubular wall having an open end and an end wall having an outlet opening at the end of the tubular wall opposite its open end, and a plunger having one end portion positioned within and sealing against the inner surface of said tubular wall and an opposite end portion projecting from the open end of said tubular wall, with the fluid being within said tubular wall between said end wall and said plunger, said device comprising:

a hose assembly having first and second ends and defining a passageway between said ends, with at least a portion of said passageway being defined by a capillary tube having a diameter of less than about 0.02 cm and a length of at least 2 cm, and including a coupler at said first end adapted for releasably attaching said hose assembly to the housing of a said syringe with the outlet opening of the syringe communicating with said passageway;

a frame comprising support means adapted for engaging and supporting said coupler;

spring means adapted for applying a uniform force against the plunger of the syringe to cause fluid within said syringe to flow through said hose assembly; and activating means for moving said spring means between a disengaged position spaced from the plunger of a said syringe attached to said coupler to afford insertion or removal of the syringe and said hose assembly, and an engaged position engaged with said plunger to apply said uniform force, said activating means including securing means for securing the syringe and the coupler of said hose assembly in said support means when said activating means positions said spring means in said engaged position.

2. A fluid dispensing device according to claim 1 wherein said hose assembly comprises a hose extending from adjacent said first end to adjacent said second end, at least a portion of said capillary tube is positioned within said hose adjacent said second end to provide said portion of said passageway, and said device includes sealing means for preventing movement of fluid around said capillary tube.

3. A fluid dispensing device according to claim 2 wherein said hose is heat shrinkable, and is shrunk into tight fitting engagement with the outer surface of said capillary tube to provide said sealing means.

4. A fluid dispensing device according to claim 2 wherein said hose assembly comprises a fitting at said second end having a through orifice communicating with said hose and a plug within said orifice with said capillary tube extending through said plug, said plug and fitting providing said sealing means.

5. A fluid dispensing device according to claim 1 wherein said capillary tube extends from adjacent said first end to adjacent said second end.

6. A fluid dispensing device according to claim 1 wherein:

said support frame includes an elongate portion extending away from said support means;

said support means are adapted to position a said syringe attached to said coupler over said elongate portion;

said spring means comprises a block mounted for movement along said elongate portion and having a surface adjacent said support means adapted to engage the plunger in a said syringe and a slide slideably mounted between said block and said support means for movement along said elongate portion with said spring means being coupled between said block and said slide for applying a constant force biasing said block toward said support means upon separation of said slide and said block; and said activating means comprises a cover adapted to enclose said block and a said syringe engaged with said coupler over said elongate portion said cover having one end pivotably mounted at the end of said elongate portion opposite said support means and being pivotable between an open position spaced from said elongate portion to afford insertion and removal of said coupler and a said syringe attached thereto and a closed position enclosing said block and the syringe with a portion of said cover providing said securing means, links coupled between said cover and said slide for moving said slide and block to a position spaced from the syringe when said cover is in its open position, and for moving said block into engagement with said syringe to separate said slide from said block and apply said uniform force upon movement of said cover to its closed position, and means for releasably latching said cover in its closed position.

7. A hose assembly having first and second ends and defining a through passageway between said ends, said hose assembly comprising a hose extending between said first and second ends, a coupler fixed to said hose at said first end adapted for releasably attaching said hose to the housing of a syringe with an outlet opening of the syringe communicating with said hose, a capillary tube having an inside diameter of less than about 0.02 centimeters and a length of at least 2 centimeters within said hose at said second end, and sealing means for preventing movement of fluid through said hose around said capillary tube.

8. A hose assembly according to claim 7 wherein said hose is heat shrinkable, and is shrunk into tight fitting engagement with the outer surface of said capillary tube to provide said sealing means.

9. A hose assembly according to claim 7 wherein said hose assembly comprises a fitting at said second end having a through orifice communicating with said hose, and a plug within said orifice with said capillary tube extending through said plug, said plug and fitting providing said sealing means.

* * * * *